US012637420B2

(12) United States Patent
Raskatov et al.

(10) Patent No.: US 12,637,420 B2
(45) Date of Patent: May 26, 2026

(54) METHOD FOR SEPARATION OF METHIONINE SULFOXIDE DIASTEREOMERS

(71) Applicants: The Regents of the University of California, Oakland, CA (US); Caltech, Pasadena, CA (US)

(72) Inventors: Jevgenij Raskatov, Santa Cruz, CA (US); Scott C. Virgil, Pasadena, CA (US)

(73) Assignees: The Regents of the University of California, Oakland, CA (US); Caltech, Pasadena, CA (US)

( * ) Notice: Subject to any disclaimer, the term of this patent is extended or adjusted under 35 U.S.C. 154(b) by 419 days.

(21) Appl. No.: 17/155,515

(22) Filed: Jan. 22, 2021

(65) Prior Publication Data

US 2021/0230110 A1 Jul. 29, 2021

Related U.S. Application Data

(60) Provisional application No. 62/965,349, filed on Jan. 24, 2020.

(51) Int. Cl.

| | |
|---|---|
| ***C07C 315/06*** | (2006.01) |
| ***B01D 15/36*** | (2006.01) |
| ***B01D 15/40*** | (2006.01) |
| ***B01D 15/42*** | (2006.01) |
| ***C07C 317/28*** | (2006.01) |

(52) U.S. Cl.

CPC .......... *C07C 315/06* (2013.01); *B01D 15/361* (2013.01); *B01D 15/40* (2013.01); *B01D 15/426* (2013.01); *C07C 317/28* (2013.01); *C07B 2200/07* (2013.01)

(58) Field of Classification Search

CPC .... B01D 15/361; B01D 15/40; B01D 15/426; C07B 2200/07; C07C 315/06; C07C 317/28; C07C 317/48; Y02P 20/54

See application file for complete search history.

(56) References Cited

PUBLICATIONS

Lavine (The Formation, Elution, and Optical Properties of the Diastereoisomeric Sulfoxides Derived from L-Methionine, Lankenau Hospital Research Institute and the Institute for Cancer Research, pp. 477-491, Published 1947) (Year: 1947).*

Holland et al. (Biocatalytic and Chemical routes to all the Sterioisomers of Methionine and Ethionine Sulfoxides, Tetrahedron: Asymmetry, 10, pp. 2833-2843, Published 1999) (Year: 1999).*

Toribio et al. (Enantiomeric Separation of Chiral Sulfoxides by Supercritical Fluid Chromatography, J. Sep. Sci., 29, pp. 1363-1372, Published 2006) (Year: 2006).*

De Klerck et al (Combined use of Isopropylamine and Trifluoroacetic Acid in Methanol-Containing Mobile Phase for Chiral Supercritical Fluid Chromatography, Journal of Chromatography A, 1234, pp. 72-79, published 2012) (Year: 2012).*

Zhu et al. (Stereospecific Electrophoretically Mediated Microanalysis Assay for Methionine Sulfoxide Resdctase Enzymes, Anal. Bioanal. Chem., 406, pp. 1723-1729, Published 2014) (Year: 2014).*

Raskatov et al. (A Facial Method for Separation of Methionine Sulfoxide Diastereomers, Structural Assignment, and DFT Analysis, Chem. Eur. J., 26, pp. 4467-4470, Published online Dec. 22, 2019) (Year: 2019).*

Ebinger et al. (Comparison of chromatographic techniques for diastereomer separation of a diverse set of drug-like compounds, J. of Chromatography A., 1272, pp. 150-154, Published 2013) (Year: 2013).*

Craig White (Integration of supercritical fluid chromatography into drug discovery as a routine support tool Part I. Fast chiral screening and purification, J. of Chromatography A, 1074, pp. 163-173, Published 2005) (Year: 2005).*

A. Drazic, et al., “The physiological role of reversible methionine oxidation”, Biochim. Biophys. Acta 2014, 1844, 1367-1382.

A. Drazic, et al., “Methionine oxidation activates a transcription factor in response to oxidative stress”, Proc. Natl. Acad. Sci. USA 2013, 110, 9493-9498.

A. Gennaris, et al., “Repairing oxidized proteins in the bacterial envelope using respiratory chain electrons”, Nature 2015, 528, 409-412.

B. C. Lee, et al., “MsrB1 and MICALs Regulate Actin Assembly and Macrophage Function via Reversible Stereoselective Methionine Oxidation”, Mol. Cell. 2013, 51, 397-404.

B. Manta, et al., “Regulated methionine oxidation by monooxygenases”, Free. Radic. Biol. Med. 2017, 109, 141-155.

D. B. Oien, et al., “Genetic regulation of longevity and age-associated diseases through the methionine sulfoxide reductase system” Biochim. Biophys. Acta Mol. Basis. Dis. 2018, 1865, 1756-1762.

E. G. Gharakhanian, et al., “Influence of Sulfoxide Group Placement on Polypeptide Conformational Stability”, J. Am. Chem. Soc. 2019, 141, 14530-14533.

E. J. Walker, et al., “Global analysis of methionine oxidation provides a census of folding stabilities for the human proteome”, Proc. Natl. Acad. Sci. USA 2019, 116, 6081-6090.

E. R. Stadtman, et al., “Cyclic oxidation and reduction of protein methionine residues is an important antioxidant mechanism”, Mol. Cell. Biochem. 2002, 234, 3-9.

(Continued)

*Primary Examiner* — Andrew D Kosar
*Assistant Examiner* — Blaine G Doletski
(74) *Attorney, Agent, or Firm* — CARTER, DELUCA & FARRELL LLP

(57) ABSTRACT

A method of separating a compound having methionine oxide diastereomers, including: loading a diastereomeric mixture into a chromatography column, the diastereomeric mixture of a compound having a plurality of methionine oxide diastereoisomers. The method also includes passing a mobile phase, the mobile phase including a supercritical fluid, through the chromatography column to separate the compound based on each methionine oxide diastereoisomer of the plurality of methionine oxide diastereoisomers in the chromatography column.

11 Claims, 3 Drawing Sheets

(56) References Cited

PUBLICATIONS

K. Ebinger, et al., "Comparison of chromatographic techniques for diastereoner separation of a diverse set of drug-like compounds", Journal of Chromatography A, vol. 1272 (2013) pp. 150-154.
G. Kim, et al., "Methionine oxidation and reduction in proteins", Biochim. Biophys. Acta 2014, 1840, 901-905.
G. P. Dado, et al., "Redox Control of Secondary Structure in a Designed Peptide", J. Am. Chem. Soc. 1993, 115, 12609-12610.
H. Sies, et al., "Oxidative Stress", Annu. Rev. Biochem. 2017, 86, 715- 48.
J. Moskovitz, "Methionine sulfoxide reductases: ubiquitous enzymes involved in antioxidant defense, protein regulation, and prevention of aging-associated diseases" Biochim. Biophys. Acta 2005, 1703, 213-219.
K. B. Wiberg, "Application Of The Pople-Santry-Segal Cndo Method To The Cyclopropylcarbinyl And Cyclobutyl Cation And To Bicyclobutane", Tetrahedron 1968, 24, 1083-1096.
L. Tarrago, et al., "Monitoring methionine sulfoxide with stereospecific mechanism-based fluorescent sensors", Nat. Chem. Biol. 2015, 11, 332-338.
M. Inoue, et al., "Total synthesis of the large non-ribosomal peptide polytheonamide B", Nat. Chem. 2010, 2, 280-285.
M. Palmblad, et al., "Oxidation of Methionine 35 Attenuates Formation of Amyloid b-Peptide 1-40 Oligomers", J. Biol. Chem. 2002, 277, 19506-19510.
N. Emmanuel, et al., "Scalable Photocatalytic Oxidation of Methionine under Continuous-Flow Conditions", Org. Process Res. Dev. 2017, 21, 1435-1438.
P. W. Skelly, et al., "Relative Rates of Metal-Free Azide-Alkyne Cycloadditions: Tunability over 3 Orders of Magnitude", J. Org. Chem. 2019, doi.org/10.1021/acs.joc.9b01887.
R. G. Midwinter, et al., "IkB is a sensitive target for oxidation by cell-permeable chloramines: inhibition of NF-KB activity by glycine chloramine through methionine oxidation", Biochem. J. 2006, 396, 71-78.
R. L. Levine, et al., "Methionine residues as endogenous antioxidants in proteins", Proc. Natl. Acad. Sci. USA 1996, 93, 15036-15040.
R. L. Levine, et al., "Methionine residues may protect proteins from critical oxidative damage", Mech. Ageing Dev. 1999, 107, 323-332.
S. Boschi-Muller, et al., "Methionine sulfoxide reductase: Chemistry, substrate binding, recycling process and oxidase activity", Bioorg. Chem. 2014, 57, 222-230.
S. Matsuoka, et al., "The effect of sulfur stereochemistry of L-b,b-dimethylmethionin", Tet. Lett. 2010, 51, 4644-4647.
T. F. Lavine, "The Formation, Resolution, And Optical Properties Of The Diastereoisomeric Sulfoxides Derived From L-Methionine", J. Biol. Chem. 1947, 169, 477-491.
T. Hoshi, et al., "Regulation of cell function by methionine oxidation and reduction," J. Physiol. 2001, 531, 1-11.

* cited by examiner

METHOD FOR SEPARATION OF METHIONINE SULFOXIDE DIASTEREOMERS

CROSS-REFERENCE TO RELATED APPLICATION

The present application claims the benefit of and priority to U.S. Provisional Patent Application No. 62/965,349, filed on Jan. 24, 2020. The entire disclosure of the foregoing application is incorporated by reference herein.

BACKGROUND

Oxidation of methionine (Met), which is shown in formula (I) below, is an important biological redox node, with thousands of protein targets.

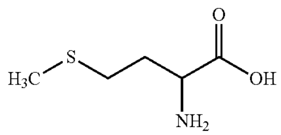

(I)

Met sulfur oxidation is an important biomolecular redox process that yields methionine sulfoxide (Met-SO) as the reaction product and may affect any Met-containing protein. Because most proteins contain at least one methionine residue, Met oxidation has a vast range of potential biomolecular targets. Biologically important examples of the Met→Met-SO reaction include regulation of cellular functions, protection of proteins from oxidative damage by providing sites that can scavenge reactive oxygen species, changes in gene transcription in response to oxidative stress, as well as oxidative damage of long-lived proteins upon aging.

The oxidation process yields Met-SO and renders the sulfur chiral, producing two distinct, diastereomerically related products. In particular, upon oxidation of Met to Met-SO, a stereogenic sulfur center is formed, and the reaction yields two diastereomers, (S,S) and (S,R) with the naturally occurring(S)-Met. The sulfur chirality of Met-SO is stable with respect to stereo-chemical inversion, and living systems have evolved enzymes, termed reductases, which are capable of stereospecifically reducing the Met-SO diastereomers back to Met. The impact of Met-SO sulfur chirality on peptide properties is strongly suggested through studies with the chemically-similar system of β,β-dimethylmethionine oxide, in which the stereoisomers are much easier to separate due to higher sidechain rigidity than that of Met-SO. Whereas the biological significance of Met-SO sulfur chirality is clearly established, chemical biology efforts to study consequences of Met→Met-SO reaction have thus far been commonly performed with mixtures of diastereomers. This is due to the challenges in obtaining diastereomerically pure Met-SO. Recent studies by Gennaris et al., *Nature* (2015), 528, 409-412 and Lavine et al., *J. Biol. Chem.* (1947), 169, 477-491 investigated the repair of oxidized proteins of the bacterial envelope using the diastereomerically resolved Met-SO diastereomers, obtained by a fractional crystallization method that was developed in 1947. Fractional crystallization of diastereomers that differ in as little as the orientation of a single methyl group may be challenging to perform reproducibly and reliably, which is the reason why this conventional method is not routinely used in the field.

Stereochemistry of Met-SO sulfur is likely to have biophysical, biochemical, and biological significance, and may affect both structural and functional properties of thousands of proteins and peptides. Thus, more research and better chemical tools are needed to advance understanding of the Met redox proteome. Despite the biological significance of Met oxidation, a reliable process for separating the resultant Met-SO diastereomers is currently lacking. This hampers synthesis of peptides and proteins that contain stereochemically defined Met-SO and study of their structural and functional properties. Thus, there is a need for separating stereochemically defined Met-SO.

SUMMARY

The present disclosure provides a novel method that uses supercritical carbon dioxide ($scCO_2$) chromatography and allows for obtaining both diastereomers of Met-SO in purities exceeding 99%. $^1H$ NMR spectra of separated Met-SO diastereomers were correlated with their X-ray structural information. The stereochemical inversion barrier at sulfur was calculated as approximately 45.2 kcal/mol, which, being about 7.4 kcal/mol higher than that of BINOL, highlights the remarkable stereochemical stability of Met-SO sulfur chirality. The disclosed process also allows for synthesis and study of a wide variety of stereochemically defined Met-SO-containing proteins and peptides, including those believed to be responsible for Alzheimer's Disease ("AD").

Most proposed AD therapeutic efforts target amyloid beta (AB), a key protein/peptide implicated in the pathogenesis of AD and mostly failed in phase III clinical trials. Aβ42 is a believed to be a key toxic agent in AD. Recently, the Aducanumab antibody that binds to aggregated Aβ42 showed some benefit in a phase III clinical trial for the first time. To develop better AD therapeutics, it will be important to advance mechanistic understanding of Aβ42 toxicity. Subtle changes arising from single D-amino acid substitutions may have a major impact on Aβ42 aggregation and toxicity. The relevance of such changes to native Aβ42 in the AD brain has nevertheless been unclear, including which residues in Aβ42 are particularly prone to chiral perturbation and are abundant in the brain.

Amyloid deposits found in AD brains are very heterogeneous, containing various Aβ42 truncation products and post-translationally modified Aβ42 variants. The presence of various products and peptides needs to be taken into account in developing better approaches to block the toxic actions of Aβ42 in AD. Aβ42 that is oxidized to sulfoxide at residue Met35 (i.e., to Aβ42-Met35SO) is particularly abundant in AD brains.

From about 10% to about 50% of Aβ42 deposited in AD brains is estimated to be Aβ42-Met35SO. It is estimated that up to approximately half of Aβ42 found in AD brains is oxidized at Met35 to Aβ42-Met35SO. Further, Aβ42-Met35SO has both reduced and enhanced fibrillogenicity relative to un-oxidized Aβ42. In addition, there is no consensus as to toxicity of Aβ42-Met35SO relative to un-oxidized Aβ42. Thus, there is a staggering degree of disagreement on the consequences of Aβ42 Met35 oxidation that is unlikely to be due to simple batch-to-batch variance or differences in cell model systems.

Methionine sulfur becomes chiral upon MetSO formation. Once formed, the chiral sulfur epimers are stereochemically stable under physiological conditions. The significance of MetSO sulfur chirality in protein function is exemplified by MICAL-driven (R)-stereoselective methionine oxidation, which mediates actin disassembly. The reverse reaction is catalyzed by methionine sulfoxide reductase (MSR) B, a stereoselective Met-(R)—SO reductase. Using the disclosed methods, MetSO chiral sulfur epimers can be produced in purities at or above 99.5% on a gram scale. From these, Aβ42-Met35SO chiral sulfur epimers were produced with no loss of stereochemical information. MSR B levels are abnormally low in AD brains. This may lead to fluctuations in the distribution of un-oxidized Aβ42, Aβ42-Met35-(R)—SO and Aβ42-Met35-(S)—SO, which could impact local peptide neurotoxicity. The compounds obtained using the methods according to the present disclosure may be used to measure distribution of the chiral sulfur epimers of MetSO in Aβ42 deposits.

The MetSO sulfur is chiral, so that two Aβ42-Met35SO peptides are formed upon Aβ42 Met35 oxidation and rather than just one. The impact of sulfur chirality on Aβ42-Met35SO structure and function appears to be unknown, as past research always studied mixtures of Aβ42-Met35SO chiral sulfur epimers.

It is hypothesized herein that Aβ42-Met35SO sulfur chirality is the variable responsible for the vast discrepancies reported on Aβ42-Met35SO behavior. There are two methionine sulfoxide reductases, which stereoselectively reduce Met-(S)—SO and Met-(R)—SO, highlighting the potential importance of sulfur chirality. Research on Aβ42-Met35SO chiral sulfur epimers has been hampered by the lack of methods to make Met-(R)—SO and Met-(S)—SO building blocks for peptide synthesis.

The present disclosure provides an innovative methodology that yields both chiral sulfur epimers on a gram scale and in purities exceeding 99.5%. Aβ42-Met35-(R)—SO and Aβ42-Met35-(S)—SO may also be synthesized without any detectable Met35SO sulfur chirality scrambling. So disclosed herein are believed to be the first synthesized pure Aβ42-Met35SO chiral sulfur epimers. These compounds allow for an understanding of the impact of Met35SO sulfur chirality upon Aβ42-Met35SO aggregation and toxicity.

According to one embodiment of the present disclosure, a method for producing a diastereomerically pure methioinine sulfoxide composition is disclosed. The method includes: loading a diastereomeric mixture including compositions containing S-methionine sulfoxide (Met-(S)—SO) or containing R-methionine sulfoxide (Met-(R)—SO) onto a chromatography column. The method also includes: passing a mobile phase, the mobile phase including a supercritical fluid, through the chromatography column to separate the Met-(S)—SO containing compositions from the Met-(R)—SO containing compositions. Compositions that can be said to "contain" Met-(S)—SO or Met-(R)—SO include Met-(S)—SO or Met-(R)—SO alone, compounds that include Met-(S)—SO or Met-(R)—SO in combination with a protecting group (such as FMOC) or peptides or proteins that include Met-(S)—SO or Met-(R)—SO (such as Aβ42).

According to an aspect of the above-embodiment, the method further includes dissolving the diastereomeric mixture in an eluent, which may be ethanol.

According to another aspect of the above-embodiment, the supercritical fluid is selected from the group consisting of carbon dioxide, nitrous oxide, ammonia, and combinations thereof. The supercritical fluid may be present from about 50% to about 60% of the mobile phase.

According to a further aspect of the above-embodiment, the mobile phase further includes a co-solvent. The co-solvent may be selected from the group consisting of methanol, isopropanol, methylene chloride, tetrahydrofuran, acetonitrile, and combinations thereof. The co-solvent may be present from about 40% to about 50% of the mobile phase.

According to yet another aspect of the above-embodiment, the mobile phase further includes an additive. The additive may be trifluoroacetic acid. The trifluoroacetic acid may be present from about 0.1% to about 0.5% of the mobile phase.

According to an aspect of the above-embodiment, a methionine oxide containing diastereoisomer of the plurality of methionine oxide containing diastereoisomers is fluorenyl methyl oxycarbonyl chloride-methionine sulfoxide.

According to another aspect of the above-embodiment, the diastereomeric mixture may include Met-(S)—SO Aβ42 and Met-(R)—SO Aβ42.

According to another embodiment of the present disclosure, a methionine sulfoxide (MetSO) composition is disclosed. The MetSO composition includes at least 60% Met-(R)—SO relative to Met-(S)—SO or comprising at least 60% Met-(S)—SO to Met-(R)—SO.

According to one aspect of the above embodiment, the MetSO composition may include at least 95% Met-(R)—SO relative to Met-(S)—SO or comprising at least 95% Met-(S)—SO to Met-(R)—SO.

According to one aspect of the above embodiment, the MetSO composition may include at least 99% Met-(R)—SO relative to Met-(S)—SO or comprising at least 99% Met-(S)—SO to Met-(R)—SO.

According to another embodiment of the present disclosure, an Aβ42 composition including MetSO at position 38 is disclosed. The Aβ42 composition may include at least 60% Met-(R)—SO relative to Met-(S)—SO or at least 60% Met-(S)—SO relative to Met-(R)—SO at amino acid 38.

According to one aspect of the above embodiment, the Aβ42 composition may include at least 90% Met-(R)—SO relative to Met-(S)—SO or at least 90% Met-(S)—SO relative to Met-(R)—SO at amino acid 38.

According to another embodiment of the present disclosure, the Aβ42 composition may include at least 95% Met-(R)—SO relative to Met-(S)—SO or at least 95% Met-(S)—SO relative to Met-(R)—SO at amino acid 38.

BRIEF DESCRIPTION OF DRAWINGS

Various embodiments of the present disclosure are described herein below with reference to the figures wherein.

DETAILED DESCRIPTION

Figure 1:
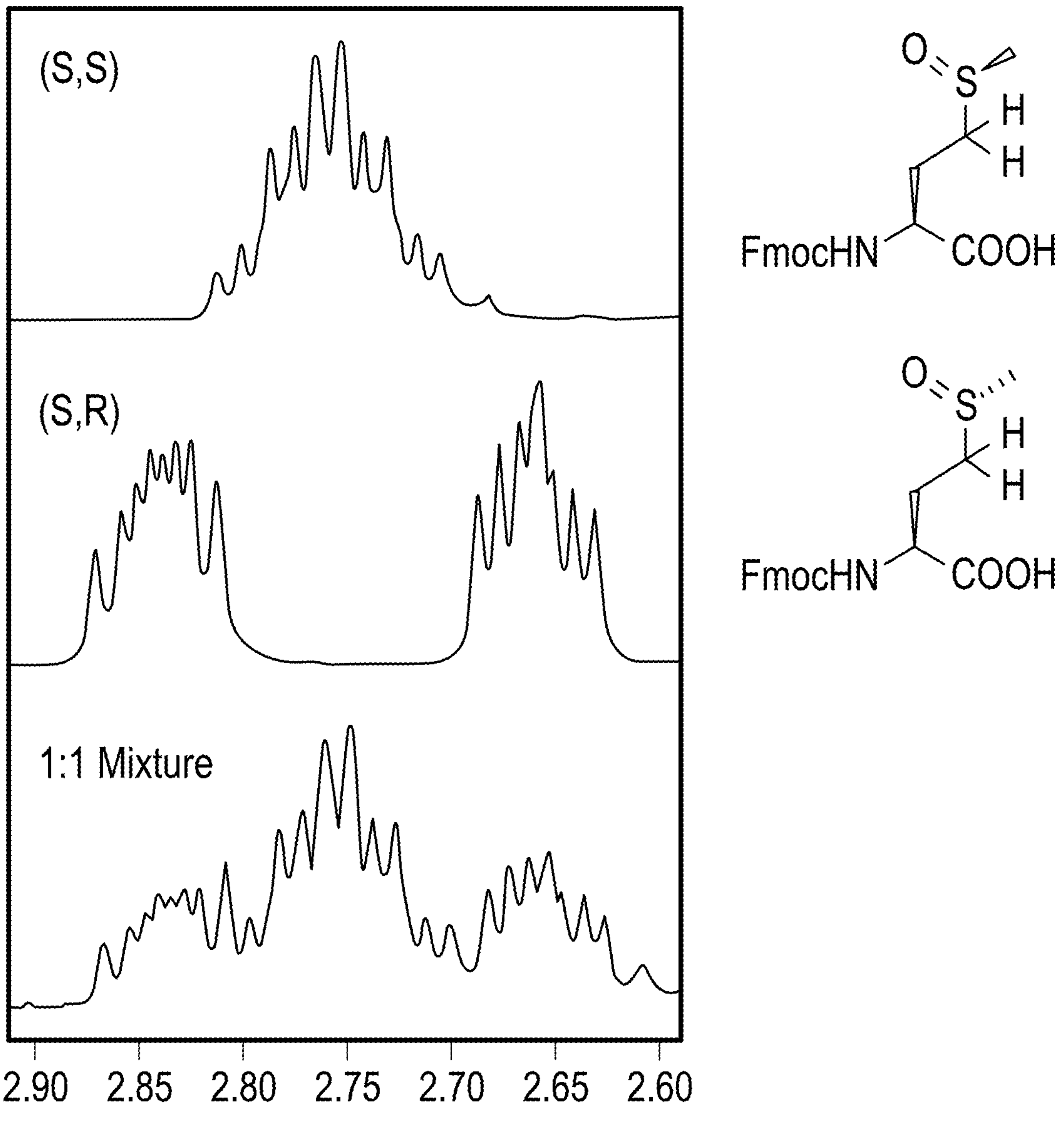
FIG. 1 is $^1$H NMR spectra of the diagnostic region of fluorenyl methyl oxycarbonyl chloride-methionine sulfoxide (Fmoc-Met-SO), with protons diagnostic for the two diastereomers indicated in an oval.

The present disclosure provides a novel supercritical fluid purification method, through which large (i.e., gram) quantities of diastereomerically pure Met-SO (larger than approximately 99% purity) are reliably and readily obtained. The access to diastereomerically pure (S,S) and (S,R)-Met-SO was used in turn to correlate $^1H$ NMR with absolute stereochemical information that was obtained using X-Ray crystal structure analysis. The activation barrier for the interconversion of the two Met-SO diastereomers was calculated using quantum chemical (DFT) methods.

Separation of the Met-SO diastereomers is challenging and standard HPLC-based purification methods or fractional crystallization approaches are unsuccessful. The disclosed method achieves baseline separation of two Met-SO diastereomers, such as fluorenyl methyl oxycarbonyl chloride-methionine sulfoxide (Fmoc-Met-SO), by employing a purification process that uses a supercritical fluid. The diastereomeric mixture, which forms a stationary phase that includes two methionine oxide diastereoisomers, may be dissolved in a solvent, i.e., eluent, such as ethanol, to form a solution. The solution may be heated and/or stirred to fully dissolve the diastereoisomers. Thereafter the solution may be purified using supercritical fluid chromatography. The solution may be loaded into an ion chromatography (IC) column such as 20×250 mm Chiral Technologies IC column and the mobile phase is supplied to the IC column.

The mobile phase may include a supercritical fluid as a solvent. As used herein supercritical fluid is a substance that is above or close to its critical temperature and pressure. Suitable supercritical fluids include carbon dioxide, nitrous oxide, ammonia, and combinations thereof. The supercritical fluid may be present in an amount from about 50% to about 60% by weight of the mobile phase. The mobile phase may also include an organic co-solvent, such as methanol, isopropanol, methylene chloride, tetrahydrofuran, acetonitrile, and combinations thereof. The co-solvent may be present in an amount from 40% to about 50% by weight of the mobile phase. Furthermore, the mobile phase may include an additive, such as trifluoroacetic acid, which may be present from about 0.1% to about 0.5% by weight of the mobile phase. After supercritical chromatography, the separated Met-SO diastereomers are then collected and recrystallized to obtain isometrically pure samples of each diastereomers. Isometric purity may be at least 60%, at least 65%, at least 70%, at least 75%, at least 80%, at least 85%, at least 90%, at least 95%, at least 99%, at least 99.5% at least 99.9%, or 100% of either of the diastereomers, namely, Met-(S)—SO or Met-(R)—SO. As used herein, isometric purity denotes amount of one of the diastereomers with the remainder being the other diastereomer.

Met-SO diastereomers may also be incorporated into any protein and peptide, such as Aβ42. In embodiments, Met-SO may be incorporated at position 38. One of the Met-SO diastereomers (i.e., Met-(S)—SO or Met-(R)—SO) may be present at amino acid 38 of Aβ42 at a purity of at least 90%. In further embodiments, one of the Met-SO diastereomers (i.e., Met-(S)—SO or Met-(R)—SO) may be present at amino acid 38 of Aβ42 at a purity of at least 60%, at least 65%, at least 70%, at least 75%, at least 80%, at least 85%, at least 90%, at least 95%, or greater than 95%.

Methionine sulfoxide has a chiral sulfur atom. Using quantum chemical approaches, the inversion barrier between Met-(R)—SO and Met-(S)—SO was calculated to be about 45.2 kcal/mol. This activation energy is sufficiently high that the two Aβ42-Met35SO diastereomers will not interconvert under physiological conditions. Thus, it is believed that Aβ42-Met35SO is a mixture of two compounds rather than just one. The method of obtaining diastereomerically pure Met-SO allowing for further study of such peptides.

The method according to present disclosure allows for incorporation of stereochemically defined, i.e., diastereomerically pure, Met-SO into any protein and peptide, which was previously challenging due to deficiencies in conventional separation methodology. The process disclosed herein may be easily adopted by academic and industrial laboratories alike and may have significant impact on the field studying methionine oxidation, which is an important node of cellular biomolecular redox chemistry. The process may be also of interest for materials scientists to explore Met-SO sulfur chirality as a structural control element that is both extremely subtle and remarkably stereochemically stable.

The following Examples illustrate embodiments of the present disclosure. These Examples are intended to be illustrative only and are not intended to limit the scope of the present disclosure. Also, parts and percentages are by weight unless otherwise indicated. As used herein, "room temperature" or "ambient temperature" refers to a temperature from about 20° C. to about 25° C. and "standard pressure" refers to a pressure about 1 atm. Unless stated otherwise, the Examples were performed at ambient temperature and standard pressure.

EXAMPLES

Example 1

This example describes separation of diastereomers of Fmoc-Met-SO using the method according to the present disclosure.

A supercritical $CO_2$-based separation method was used for separating Fmoc-MetSO diastereomers, which allowed for production of gram quantities of the Fmoc-Met-(R)—SO and Fmoc-Met-(S)—SO diastereomers in purities at or above 99.5%. Alternative methods to obtain Fmoc-MetSO diastereomers are much more elaborate and do not yield material that is nearly as pure, and small impurities can lead to pronounced changes in Aβ42 properties.

Baseline separation of the two Fmoc-Met-SO diastereomers was achieved by employing a purification process that uses supercritical $CO_2$. The diastereomeric mixture of Fmoc-Met-SO was dissolved in ethanol under gentle heating. The mixture was purified in a 20×250 mm Chiral Technologies IC column on a JASCO System 2000 preparative SFC system at a flow rate of about 30 mL/min of a mobile phase which included 42% isopropyl alcohol (containing 0.4% TFA) and supercritical $CO_2$. Samples were the recrystallized (fraction 1: dichloromethane/ether; fraction 2: isopropanol/ether), providing gram quantities of the two Fmoc-Met-SO diastereomers in purities exceeding 99%. The method represented a significant advance compared with fractional crystallization. In particular, the purity of the (S,R)-Fmoc-Met-SO diastereomer obtained by the present method is substantially higher than that achieved by fractional crystallization in the past, where the other diastereomer is still clearly observed by $^1H$ NMR.

Example 2

This example describes $^1H$ NMR analysis of the samples obtained using the method of Example 1.

The purified separated samples were subjected to $^1H$ NMR experiments, which were conducted with the approximately 1:1 mixture of the two Fmoc-Met-SO diastereomers. The experiments revealed that the γ-$CH_2$ group of the Met-SO sidechain was well-differentiated between the two diastereomers as shown in a bottom plot of FIG. 1 and could therefore be used as the diagnostic region to study such mixtures. The two separated Fmoc-Met-SO diastereomers were determined to be diastereomerically pure using this set of $^{1}H$ NMR signals (as shown in top and middle plots of FIG. 1), and the $^{1}H$ NMR resonances unambiguously assigned by $^{1}H$-COSY NMR spectroscopy. The diastereotopic γ-$CH_2$ protons are well-dispersed in the (S,R) diastereomer (middle plot of FIG. 1) and exhibit the expected ddd coupling pattern as a consequence of coupling with three chemically inequivalent protons. In the (S,S) diastereomer, the two γ-$CH_2$ protons are overlapped (FIG. 1, top), leading to a higher complexity peak shape due to partial overlap of two signals with ddd coupling pattern.

Example 3

This example describes X-ray crystallography analysis of the samples obtained using the method of Example 1.

X-Ray quality single crystals of the Fmoc-Met-SO diastereomer that eluted in fraction 2 in the $scCO_2$ separation procedure (top plot of FIG. 1) were grown by recrystallization from isopropanol with heating at reflux and subsequent slow cooling to room temperature.

Figure 2:
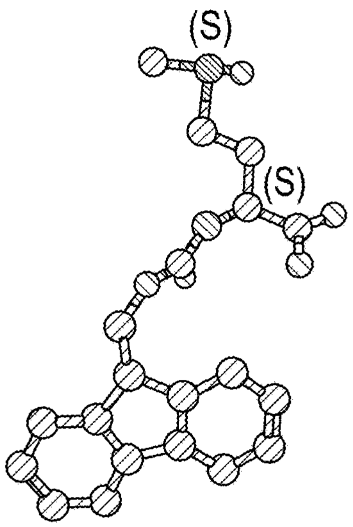
FIG. 2 is a crystal structure of the (S,S)-Fmoc-Met-SO diastereomer eluted as fraction 2 in $scCO_2$ separation.

Crystallographic structural analysis allowed the compound to be unambiguously assigned as the (S,S) diastereomer of Fmoc-Met-SO (FIG. 2).

To gain quantitative insights into the inversion barrier associated with the stereochemical inversion at the chiral Met-SO sulfur, DFT calculations were conducted. The crystallographically obtained (S,S)-Fmoc-Met-SO was fully geometry-optimized (Gaussian 09, M062X/6-311++G**). Sulfur chirality was subsequently inverted by adjusting the angles associated with the corresponding oxygen orientation accordingly. The resultant structural guess was then fully re-optimized, yielding the (S,R)-Fmoc-Met-SO diastereomer. The two Fmoc-Met-SO diastereomers were found to be nearly isoenergetic, with a marginal preference of about 0.5 kcal/mol for the (S,R) diastereomer. Transition state for the chirality inversion of the Met-SO sulfur was subsequently located using the QST3 transition state search procedure, and found to be about 45.2 kcal/mol uphill of the (S,R) diastereomer, which is consistent with the high stereochemical stability of the Met-SO diastereomers. For comparison, BINOL, which is a common example for atrop-isomerism and a stereochemically highly stable scaffold, was calculated to have a stereochemical inversion barrier of about 37.8 kcal/mol, which is about 7.4 kcal/mol lower than the barrier of stereochemical inversion at Met-SO sulfoxide.

Figure 3:
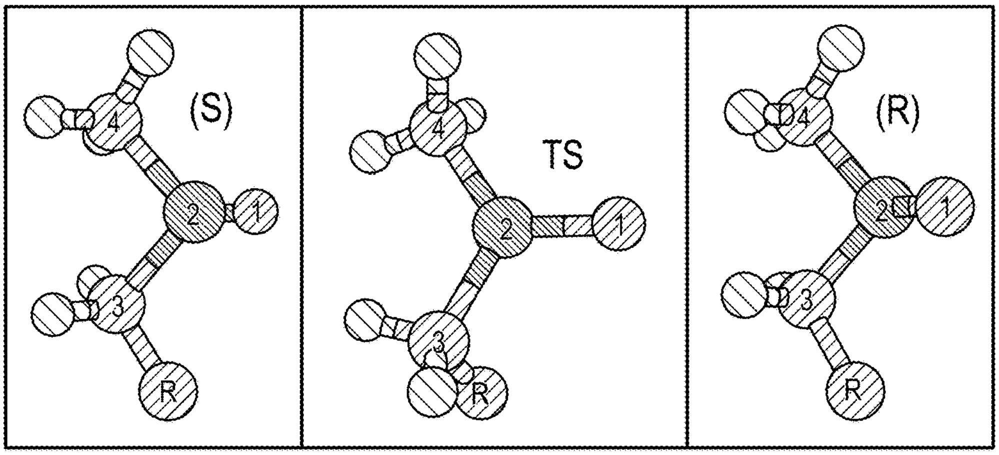
FIG. 3 shows density functional theory (DFT)-optimized partial structures of (S,S)-Fmoc-Met-SO (left), the transition state (TS) for stereochemical inversion at sulfur (middle) and (S,R)-Fmoc-Met-SO (right)

Sulfur planarization that occurs upon transition from the (S,S) to the (S,R) diastereomer (and vice versa) was calculated to produce a marginal elongation of the sulfur-oxygen bond distance from about 1.51 angstroms (Å) in the two minima to about 1.54 Å in the transition state as shown in Table 1, which lists key geometric parameters associated with the stereochemical inversion at the stereogenic sulfur of Met-SO. The two Fmco-Met-SO diastereomers are denoted as (S,S) and (S,R), respectively, and the transition state is denoted as TS. All distances are listed in [Å]; all angles and dihedral angles are listed in [°]. Atom numbering scheme used is shown in FIG. 3. Wiberg Bond Index of the S═O bond ($WB_{S=O}$) was obtained from a natural population analysis. All calculations were performed at the M062X/6-311++G** level of theory. $\Delta_{HOMO-LUMO}$ in a.u.

TABLE 1

| | 1-2 | 1-2-3 | 1-2-4 | 1-2-3-4 | $WBI_{S=O}$ | $\Delta_{HOMO-LUMO}$ |
|---|---|---|---|---|---|---|
| (S,S) | 1.51 | 105.8 | 106.5 | −109.2 | 1.22 | 0.2569 |
| TS | 1.54 | 120.9 | 121.6 | −179.5 | 1.19 | 0.2110 |
| (S,R) | 1.51 | 105.6 | 106.3 | 108.95 | 1.22 | 0.2571 |

Since the changes in bond length do not always correlate with changes in bond strength, a Wiberg bond index analysis was conducted. This analysis yielded quantitative measures of bond strength. Wiberg bond index calculations revealed that the associated changes in bond strength are minor between the two minima (WBI=1.22 for both (S,S)- and (S,R)-Met-SO) and the transition state (WBI=1.19), indicating a marginal weakening of the S═O bond in the transition state. As expected, sulfur planarization lead to an increase of the bond angles 1-2-3 and 1-2-4 from about 106° in the two minima to about 120° in the transition state. The dihedral angles 1-2-3-4 of (S,S)- and (S,R)-Met-SO were near-identical in magnitude, but with opposite signs, as expected for a local mirror image topology. Noteworthy were the changes in the $\Delta_{HOMO-LUMO}$ from 0.2569 a.u. and 0.2571 a.u. in (S,S)-Met-SO and (S,R)-Met-SO, respectively, to about 0.2110 a.u. in the transition state, reflective of the pronounced electronic changes associated with the stereochemical inversion at sulfur, and further confirming the predominantly electronic nature of the unusually high inversion barrier.

Figure 4:
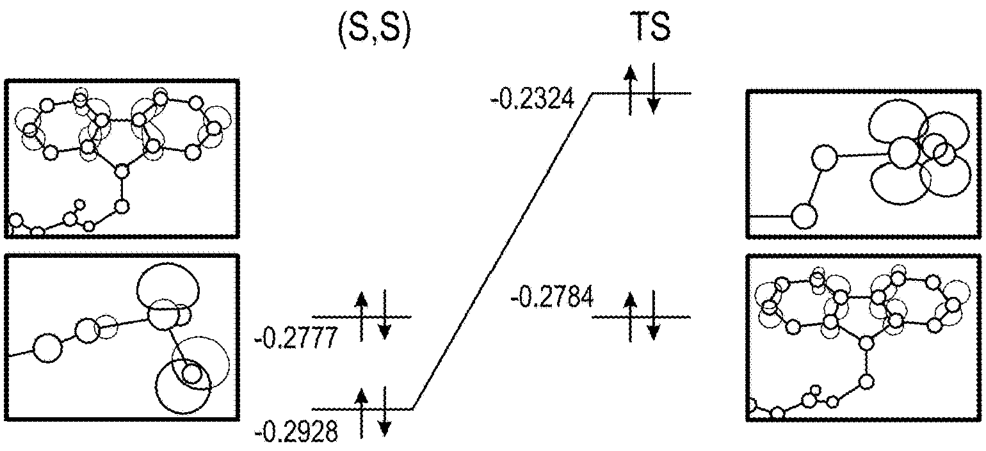
FIG. 4 is HOMO and HOMO-1 analysis for the (S,S)-Met-SO diastereomer (left) and the transition state (right)

To better understand the nature of changes in electron structure between a minimum (S,S) and the transition state, the frontier orbital analysis was also performed. The orbital relevant for the transition was HOMO-1 in the ground state and HOMO in the transition state as shown in FIG. 4. The re-hybridization of the sulfur lone pair in (ground state) to a p-type orbital (transition state) had an associated change in energy from about −0.2928 a.u. to about −0.2324 a.u., which corresponds to approximately 37.9 kcal/mol and is about 83.85% of the activation barrier calculated for the inversion of about 45.2 kcal/mol.

Example 4

This example describes synthesis of pure Aβ42-Met35-(R)—SO, Aβ42-Met35-(S)—SO chiral sulfur epimers using Fmoc-MetSO diastereomers of Example 1.

Figure 5:
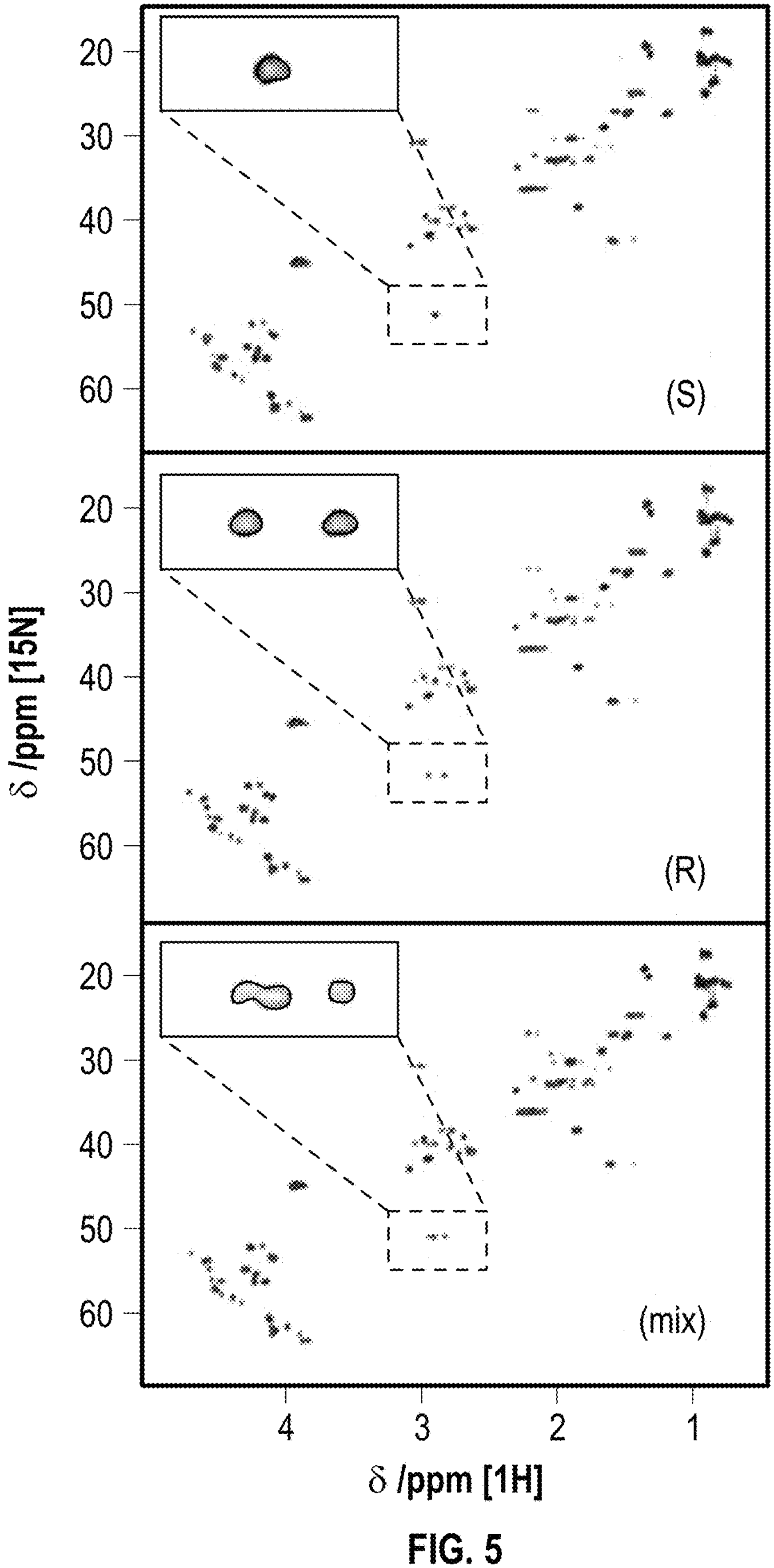
FIG. 5 shows $^1$H, $^{13}$C-HSQC NMR plots of Aβ42-Met35-(S)—SO, Aβ42-Met35-(R)—SO, and mixture thereof.

The Fmoc-MetSO diastereomers were used to make chiral sulfur epimers of Aβ42-Met35SO, as well as their diastereomer mixture. All compounds were made in purities at or above 97%. It was determined by PICUP that Aβ42-Met35SO resembles Aβ4240 in its oligomerization profile. It was found that Aβ42-Met35SO was more soluble than un-oxidized Aβ42. This facilitated NMR experiments due to the relatively poor solubility of Aβ42 (approximately 0.16 mM). A typical working concentration was about 0.32 mM of diastereomerically pure Aβ42-Met35SO, S or R) and 0.5 mM (mixture of Aβ42-Met35SO diastereomers). $^{1}H$, $^{13}C$-HSQC NMR experiments were performed which identified the γ-protons of the Met35SO sidechain as shown in FIG. 5. As can be seen, Aβ42-Met35-(S)—SO (top) and Aβ42-Met35-(R)—SO (middle) retained the signal structure observed with the Fmoc-Met-(S)—SO and Fmoc-Met-(R)—SO as shown in FIG. 1. The spectra of each of the two Aβ42-Met35SO chiral sulfur epimers showed no evidence of impurities from the other diastereomer. This validated that the disclosed methods do not induce sulfur chirality scrambling upon Aβ42 peptide synthesis to any significant degree.

The mixture of the Aβ42-Met35SO diastereomers had both signal sets present, as expected. So, it was determined unambiguously that the pure Aβ42-Met35-(S)—SO and Aβ42-Met35-(R)—SO chiral sulfur epimers can be made with no loss of stereochemical information.

It will be appreciated that of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. A method for producing a diastereomerically pure methionine sulfoxide composition, the method comprising:
- loading a diastereomeric mixture of compositions that contain S-methionine sulfoxide (Met-(S)—SO) Aβ42 and R-methionine sulfoxide (Met-(R)—SO) Aβ42 onto a chromatography column; and
- passing a mobile phase, the mobile phase including a supercritical fluid, through the chromatography column to separate the compositions that contain Met-(S)—SO Aβ42 from those that contain Met-(R)—SO Aβ42 using the chromatography column, thereby producing the diastereomerically pure methionine sulfoxide composition.

2. The method according to claim 1, further comprising: dissolving the diastereomeric mixture in an eluent.

3. The method according to claim 2, wherein the eluent is ethanol.

4. The method according to claim 1, wherein the supercritical fluid is selected from the group consisting of carbon dioxide, nitrous oxide, ammonia, and combinations thereof.

5. The method according to claim 1, wherein the supercritical fluid is present from about 50% to about 60% of the mobile phase.

6. The method according to claim 1, wherein the mobile phase further includes a co-solvent.

7. The method according to claim 6, wherein the co-solvent is selected from the group consisting of methanol, isopropanol, methylene chloride, tetrahydrofuran, acetonitrile, and combinations thereof.

8. The method according to claim 6, wherein the co-solvent is present from about 40% to about 50% of the mobile phase.

9. The method according to claim 6, wherein the mobile phase further includes an additive.

10. The method according to claim 9, wherein the additive is trifluoroacetic acid.

11. The method according to claim 10, wherein the trifluoroacetic acid is present from about 0.1% to about 0.5% of the mobile phase.

* * * * *